United States Patent [19]

Bowes et al.

[11] 4,018,831
[45] Apr. 19, 1977

[54] PRODUCTION OF 2-ETHYL HEXANAL

[75] Inventors: Emmerson Bowes, Glassboro, N.J.;
Robert E. Chute, Erie, Pa.

[73] Assignee: Mallinckrodt, Inc., St. Louis, Mo.

[22] Filed: Sept. 11, 1975

[21] Appl. No.: 612,679

[52] U.S. Cl. .................................. 260/601 R
[51] Int. Cl.$^2$ .................................. C07C 47/02
[58] Field of Search .......................... 260/601 R

[56] References Cited

UNITED STATES PATENTS

| | | | |
|---|---|---|---|
| 3,449,435 | 6/1969 | Kudu et al. | 260/593 |
| 3,903,171 | 9/1975 | Toussaint et al. | 260/601 R |

*Primary Examiner*—Bernard Helfin
*Assistant Examiner*—W. B. Lone
*Attorney, Agent, or Firm*—Carroll F. Palmer

[57] ABSTRACT

2-Ethyl hexanal is produced by hydrogenation of 2-ethyl hexene-2-al-1 without substantial formation of by-product 2-ethyl hexanol by liquid phase upflow through a catalyst bed with controlled hydrogen concentration at 90°–180° C and a pressure of 5–40 Kgm/cm$^2$.

2 Claims, No Drawings

PRODUCTION OF 2-ETHYL HEXANAL

BACKGROUND OF THE INVENTION

1. Field of the Invention

This invention relates to the production of 2-ethyl hexanal by hydrogenation of 2-ethyl hexene-2-al-1. It involves the discovery that the hydrogenation may be accomplished without producing 2-ethyl hexanol as a byproduct by using liquid phase upflow through a catalyst bed under controlled hydrogen concentration and reaction conditions.

2. Description of the Prior Art

Unsaturated carbonyl compounds can be produced on an industrial scale by aldolization processes, e.g., see U.S. Pat. No. 3,248,428. Dimerization of butyraldehyde in this manner followed by dehydration of the condensation product produces 2-ethyl hexene-2-al-1 (TEH). The present invention utilizes TEH prepared in this or any other manner for the production of 2-ethyl hexanal.

When unsaturated carbonyl compounds, e.g., $\alpha$-$\beta$ unsaturated aldehydes, are hydrogenated either the olefinic unsaturation may be saturated, the carbonyl group may be reduced or both reactions may occur. For production of saturated carbonyl compound from the unsaturated analog there has been employed either catalytic liquid phase hydrogenation process (see U.S. Pat. No. 3,272,873) or vapor phase hydrogenation process that has strong activity for olefinic hydrogenation (see U.S. Pat. No. 3,278,605). Palladium catalysts are known to have a strong activity for hydrogenating olefinic unsaturation (see U.S. Pat. No. 3,280,192).

It is also known that the hydrogenation of the unsaturated carbonyl compounds may simultaneously produce saturated carbonyl compounds and saturated alcohol, e.g., 2-ethyl hexanal and 2-ethyl hexanol from TEH (see U.S. Pat. No. 3,449,435).

Although anhydrous, or substantially anhydrous, reaction systems are more generally employed in hydrogenations as outlined above, aqueous systems have also been disclosed as useful to saturate the olefinic group without reduction of the carbonyl function (see U.S. Pat. No. 3,185,757).

Palladium catalysts and other having selected activity for olefinic unsaturation hydrogenation are generally expensive and often subject to poisoning by trace impurities. Furthermore, processes designed to saturate the olefinic group in unsaturated carbonyl compounds without reduction of the carbonyl function frequently fail to produce high conversions to the desired product, even when selected activity catalysts are involved. Accordingly, there is a need, notwithstanding the state of development of the art, for improvements in the selective hydrogenation of unsaturated aldehydes to saturated aldehydes and, specifically, conversion of TEH to 2-ethyl hexanal.

OBJECTS

A principal object of this invention is the provision of improvements in the production of 2-ethyl hexanal. Further objects include the provision of:

1. New methods for converting TEH to 2-ethyl hexanal with high selectivity relative to by-product conversion to 2-ethyl hexanol.
2. Hydrogenation procedures for converting TEH to 2-ethyl hexanal which do not require catalysts having high selectivity for olefinic unsaturation hydrogenation.
3. Such methods that produce high yields of 2-ethyl hexanal.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by a process for the production of 2-ethyl hexanal which comprises:

A. providing a bed of particulate hydrogenation catalyst,

B. passing substantially anhydrous liquid comprising 2-ethyl-hexene-2-al-1 (TEH) upwardly through said bed at a liquid hourly space velocity (LHSV) from about 0.5 to 3, C. providing hydrogen in said liquid in a concentration of about 2 to 3 mols of hydrogen per mol of TEH therein, D. maintaining the temperature of the catalyst bed at about 90°–180° C, E. maintaining the fluid in contact with said catalyst bed at a pressure between about 7 to 35 Kgm/cm$^2$, and F. recovering 2-ethyl hexanal from the over-head effluent stream from said catalyst bed.

Concentration of hydrogen in the process is controlled by (a) control of the catalyst bed D/A ratio or (b) incremental introduction of hydrogen as will be explained below in more detail.

The liquid reaction mixture charged to the catalyst bed by liquid phase upflow is preferably a solution of TEH in an inert solvent, e.g., a 10–30% solution in 2-ethyl hexanol. Various known catalysts may be used, e.g., palladium coated or suspended on a carrier, but nickel metal combined with alumina has been found to produce unique results.

DESCRIPTION OF PREFERRED EMBODIMENTS

The following details of operations in accordance with the invention and the reported data illustrate the futher principles and practice of the invention. In these specific examples and throughout the remaining specification and claims, all parts and percentages are by weight unless otherwise specified.

EXAMPLE 1

Catalyst Preparation

A solution of nickel nitrate containing 0.038 g. Ni/ml. (3430 ml.) was mixed with good agitation with 1500 ml. of aqueous solution containing 103 g. sodium aluminate, 75.5 g NaOH and 1.82 g. Na$_2$Co$_3$ at ambient temperature (20–15° C). At the completion of the precipitation, the supernatant liquor was removed by filtration and the filter cake was washed six times, each with a liter of water. The washed filter cake was then dried at 110° C and calcined at 350° C. The final powder was blended with 3% ground graphite and formed into slugs in a tablet press. The slugs were granulated and tableted in a commerical tablet press to form 4.8 ×

4.8 mm. cylinders. The cylinders were heated to 375° C in nitrogen and reduced in a flow of hydrogen gas at 435+ C. The reduced cylinders were then cooled to ambient temperature and stabilized by introduction of a steam of nitrogen containing 0.1% $O_2$ and then continuously increasing the oxygen concentration until no further exotherm occurred, the rate of increase of oxygen concentration being controlled to limit the temperature ot a maximum of 65° C. The catalyst is designated herein as "Ni Calsicat".

In another case, catalyst was prepared using the same procedure except that the 3430 ml. of nickel nitrate solution contained 25.1 g. of zinc acetate dihydrate dissolved therein. The resulting catalyst is referred to herein as Ni Calsicat Special and is designed to be resistant to poisoning by sulfur in contact with feed streams that might contain minor amounts of sulfur compounds.

EXAMPLE 2

2-ethyl hexanal Production

A circular bed of Ni Caliscat catalyst of Ex. 1 having a depth to diameter ratio of 2.5 was prepared by loading a cylindrical reactor, equipped with inlet and outlet tubes, to the required depth.

A feed stream consisting of 14% 2-ethyl hexen-2-al-1 and 86% 2-ethyl hexanol was pumped into the reactor at a rate to provide a liquid hourly space velocity (LHSV) of 1.1 through the reactor. The outlet tube was throttled to create a pressure of aproximately 35 Kgm/cc. and the temperature was adjusted by external heating jacket to approximately 95° C. Hydrogen gas under sufficient pressure to enter the feed stream was injected through the reactor inlet tube to give a 2.7:1 ratio of mols of hydrogen:mol of TEH in the feed stream. When the reactor has reached a steady state, the effluent stream from the reactor was collected and then separated into its components, i.e., TEH, 2-ethyl hexanal and 2-ethyl hexanol. This separation produced the following data:
TEH converted — 74%
Product as 2-ethyl hexanal — 97.5%
Product as 2-ethyl hexanol — 2.5%

EXAMPLE 3

Modifications of Example 2

The procedure of Ex. 2 was repeated with the following changes:
LHSV — 1.6
Reactor temperature — 120° C
Mols $H_2$/mol TEH — 2.9:1
Separation of the effluent stream as in Ex. 2 produced the following data: TEH converted — 88%
Product as 2-ethyl hexanal — 94%
Product as 2-ethyl hexanol — 6%
In another case the Ni Calsicat Special catalyst of Ex. 1 was used instead of Ni Calsicat. The results were not appreciably different from those reported above.

EXAMPLE 4

Comparison Procedure

The reactor loaded as reported in Ex. 2 with catalyst was operated in reverse, i.e., feed stream was fed downwardly so the reactor operated as a trickle bed with an LHSV of 1.5. Also the reactor was saturated with hydrogen giving a mols $H_2$/mol TEH ratio of 160:1. Separation of the reaction mixture produced the following data:
TEH converted — 89%
Product as 2-ethyl hexanal — 0.1%
Product as 2-ethyl hexanol — 99.9%

DISCUSSION OF DETAILS

The success of the present invention is due, in part, to the discovery that in hydrogenation of TEH to 2-ethyl hexanal using liquid phase upflow through a catalyst bed under controlled hydrogen concentration and reaction conditions as described herein, high yields of 2-ethyl hexanal without substantial by-product 2-ethyl hexanol can be obtained with a wide variety hydrogenation catalysts, i.e., the new procedures are not dependent on catalysts known to be specific for olefinic unsaturation reduction as opposed to carbonyl function reduction. Of course, such specific type catalysts may be used, e.g., palladium metal catalysts, particularly those using carbon or alumina as a carrier for Pd metal. Unique results have been obtained in the new methods using nickel-alumina catalysts, particularly such catalysts formed by coprecipitation of Ni metal, oxide or hydroxide and aluminum hydroxide followed by dehydration, calcination and oxidation to provide a Ni/Al$_2O_3$ ratio of between 2:8 and 8.2. Other hydrogenation catalysts may be used, including cobalt, platinum, tungsten and molybdenum metal and oxides, salts, alloys and complexes thereof.

The catalysts should be in particulate form for use in the new methods, e.g., pellets, rings, slugs, discs and other molded shapes or irregular particles. They should have an average particle size of between about 1 to 25 mm., i.e., from a No. 18 to 1 inch U.S. standard sieve series size. Preferred particle size is 4 to 12.7 mm., i.e., No. 5 to ½ inch sieve series size.

In an embodiment of the invention, a catalyst is used which carries the active catalyst agent, e.g., Ni metal, on the periphery of the catalyst particles so that the slower carbonyl function reduction reaction will not take place in the inner pores of the catalyst. Alternatively, a catalyst having porosity large enough as not to limit diffusion of reactants and products may be employed.

It is possible to use undiluted TEH as the reaction liquid in the new methods. Preferably, however, a solution of TEH in an inert, anhydrous solvent is used. Although 2-ethyl hexanol is preferred as the solvent, others may be used, e.g., pentanol, cyclohexanol, hexahydrocumene, diamyl ether, 1,2 - dichlorobenzene, etc. The concentration of TEH in such solution may be about 5 – 95% and preferably 10 – 30%.

The new hydrogenation processes may be conducted in any form of equipment in which a bed of the catalyst particles may be formed for continuous liquid phase upward flow of reaction liquid through the catalyst bed at a liquid hourly space velocity (LHSV) of between 0.5 – 3 and preferably 1.0 – 1.5. A cylinderical catalyst reactor is advantageously used, but a columnar reactor of square, rectangular or other cross-sectional shape may be employed. The equipment should include valved inlets and outlets together with pump means to provide a liquid pressure of between about 7 to 35 K gm./cm$^2$ within the catalyst bed. The equipment may be structured so that the hydrogenation is conducted with the catalyst bed in a fluidized state.

The temperature of the reaction liquid passing through the catalyst bed should be about 90° – 180° C and preferably 90° – 120° C. The equipment should be provided with suitable heating means, e.g., external steam jacket, electrical resistance heaters, etc., to heat the catalyst bed and maintain it at such temperature.

The concentration of hydrogen in the liquid passing through the catalyst bed should be controlled to be slightly in excess of the stoichiometric requirement, preferably between about 2 to 3 mols of hydrogen per mol of TEH present in the reaction liquid. In one embodiment, this control is achieved by limiting the D/A ratio of the bed to between about 1:1 and 6:1, D being the depth of the bed in centimeters and A being the cross-sectional area in square centimeters and introducing hydrogen into the reaction liquid prior to contact with the catalyst bed to provide the aforesaid 2 – 3 mols $H_2$/per mol TEH ratio. In the case of a cylinderical reactor and catalyst bed, the bed would have a D/d ratio of 1:1 to 5:1, D being the depth of the bed and d the diameter, both measured in centimeters.

In another embodiment, the hydrogen concentration is controlled by incremental introduction of hydrogen vertically along the catalyst bed. In such case, the bed can have a D/A ratio in excess of 6:1 and side entering inlets spaced vertically along the columnar reactor are used to introduce hydrogen gas under the reaction pressure into the reactor to provide the stated hydrogen concentration in the reaction liquid as it flows upwardly through the catalyst bed.

We claim:
1. A process for the production of 2-ethyl hexanal without substantial simultaneous production of 2-ethyl hexanol which consists essentially of:
    A. providing a bed of particulate hydrogenation catalyst consisting essentially of nickel coated on alumina, the D/A ratio of said bed being between about 1:1 and 6:1 wherein D is the depth of the bed in centimeters and A is the cross-sectional area in square centimeters,
    B. passing 2-ethyl-hexene-2-al-1 (TEH) in the liquid phase upwardly through said bed at a LHSV from about 0.5 to 3,
    C. injecting hydrogen into stream of TEH entering said bed at the base thereof,
    D. maintaining the temperature of said bed at about 90° – 180° C,
    E. maintaining the fluid in contact with said bed at a pressure between about 7 to 35 Kgm/cm$^2$,
    F. removing a liquid stream overhead from said bed, and
    G. recovering 2-ethyl hexanal from said overhead effluent stream.
2. The process of claim 1 wherein said catalyst has an average particle size between about 1 to 25 mm.

* * * * *